United States Patent [19]

Kovacs et al.

[11] Patent Number: 5,738,627
[45] Date of Patent: Apr. 14, 1998

[54] BI-VENTRICULAR CARDIAC ASSIST DEVICE

[75] Inventors: Stephen G. Kovacs; James E. Lowe, both of Durham, N.C.

[73] Assignee: Duke University, Durham, N.C.

[21] Appl. No.: 784,130

[22] Filed: Jan. 15, 1997

Related U.S. Application Data

[63] Continuation-in-part of Ser. No. 655,310, May 21, 1996, which is a continuation of Ser. No. 292,726, Aug. 18, 1994, abandoned.

[51] Int. Cl.$^6$ ................................................. A61M 1/10
[52] U.S. Cl. ................................................. 600/16
[58] Field of Search ................................ 600/16, 17, 18

[56] References Cited

U.S. PATENT DOCUMENTS

| | | |
|---|---|---|
| 2,826,193 | 3/1958 | Vineberg . |
| 3,034,501 | 5/1962 | Hewson . |
| 3,053,249 | 9/1962 | Smith . |
| 3,233,607 | 2/1966 | Bolie . |
| 3,279,464 | 10/1966 | Kline . |
| 3,371,662 | 3/1968 | Heid et al. . |
| 3,376,863 | 4/1968 | Kolobow et al. . |
| 3,455,298 | 7/1969 | Anstadt . |
| 3,478,737 | 11/1969 | Rassman . |
| 3,587,567 | 6/1971 | Schiff . |
| 3,590,815 | 7/1971 | Schiff . |
| 3,613,672 | 10/1971 | Schiff . |
| 4,048,990 | 9/1977 | Goetz . |
| 4,192,293 | 3/1980 | Asrican . |
| 4,506,658 | 3/1985 | Casile . |
| 4,536,893 | 8/1985 | Parravicini . |
| 4,621,617 | 11/1986 | Sharma . |
| 4,690,134 | 9/1987 | Snyders . |
| 4,731,076 | 3/1988 | Noon et al. . |
| 4,809,684 | 3/1989 | Gardner et al. . |
| 4,922,893 | 5/1990 | Wright et al. . |
| 5,119,804 | 6/1992 | Anstadt . |
| 5,169,381 | 12/1992 | Snyders . |
| 5,273,518 | 12/1993 | Lee et al. . |
| 5,429,584 | 7/1995 | Chiu . |

FOREIGN PATENT DOCUMENTS

| | | |
|---|---|---|
| 2 321 266 | 3/1977 | France . |
| 0200117 | 7/1967 | U.S.S.R. . |

OTHER PUBLICATIONS

Wolcott and Wherry, Surgery, Nov., 1960, pp. 903–906, 601/153.

Primary Examiner—Scott M. Getzow
Attorney, Agent, or Firm—Nixon & Vanderhye PC

[57] ABSTRACT

A bi-ventricular cardiac assist device maintains blood circulation in a patient having a minimally functioning or malfunctioning heart. The biventricular cardiac assist device includes a self-supporting cup-shaped outer shell having opposed upper and lower ends, and an inner surface which establishes an interior cavity for receiving a heart therein. The outer shell defines a pair of diametrically opposed slots oriented generally longitudinally between the upper and lower ends of the outer shell. An annular diaphragm conformably shaped to the outer shell is positioned adjacent to the outer shell's inner surface. The diaphragm most preferably includes upper and lower edges bonded to the outer shell at the upper and lower ends thereof, and a pair of diametrically opposed, generally longitudinally oriented unitary connection flange. Each connection flange is preferably generally T-shaped in cross-section and coupled to a respective one of the slots. The connection flanges are thus bonded to the outer shell so that the diaphragm defines a pair of semi-annular fluid chambers with the inner surface of said outer shell. Most preferably, all structural components, e.g., the outer shell and the diaphragm, are formed of substantially the same urea-linked polyureathane copolymer, but have different Shore A hardness values.

39 Claims, 3 Drawing Sheets

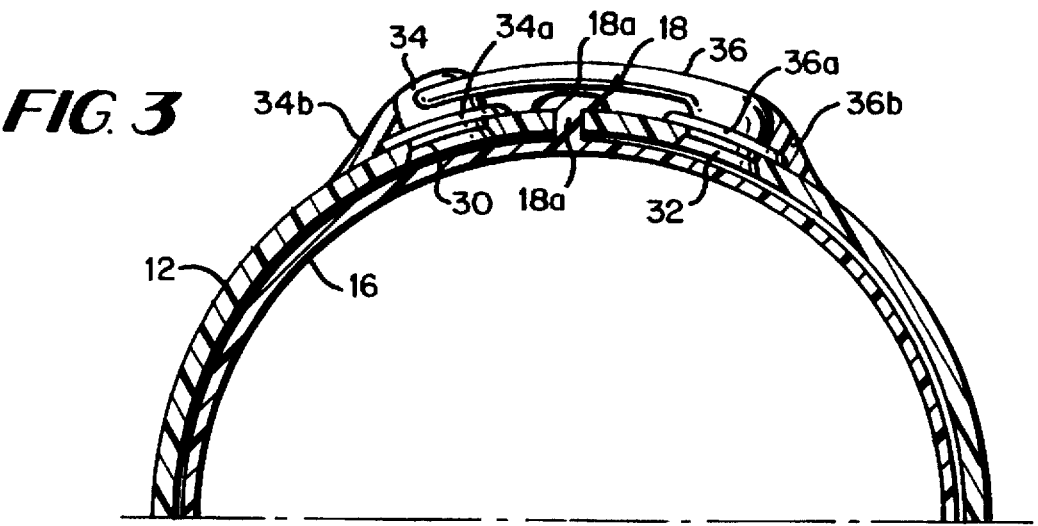
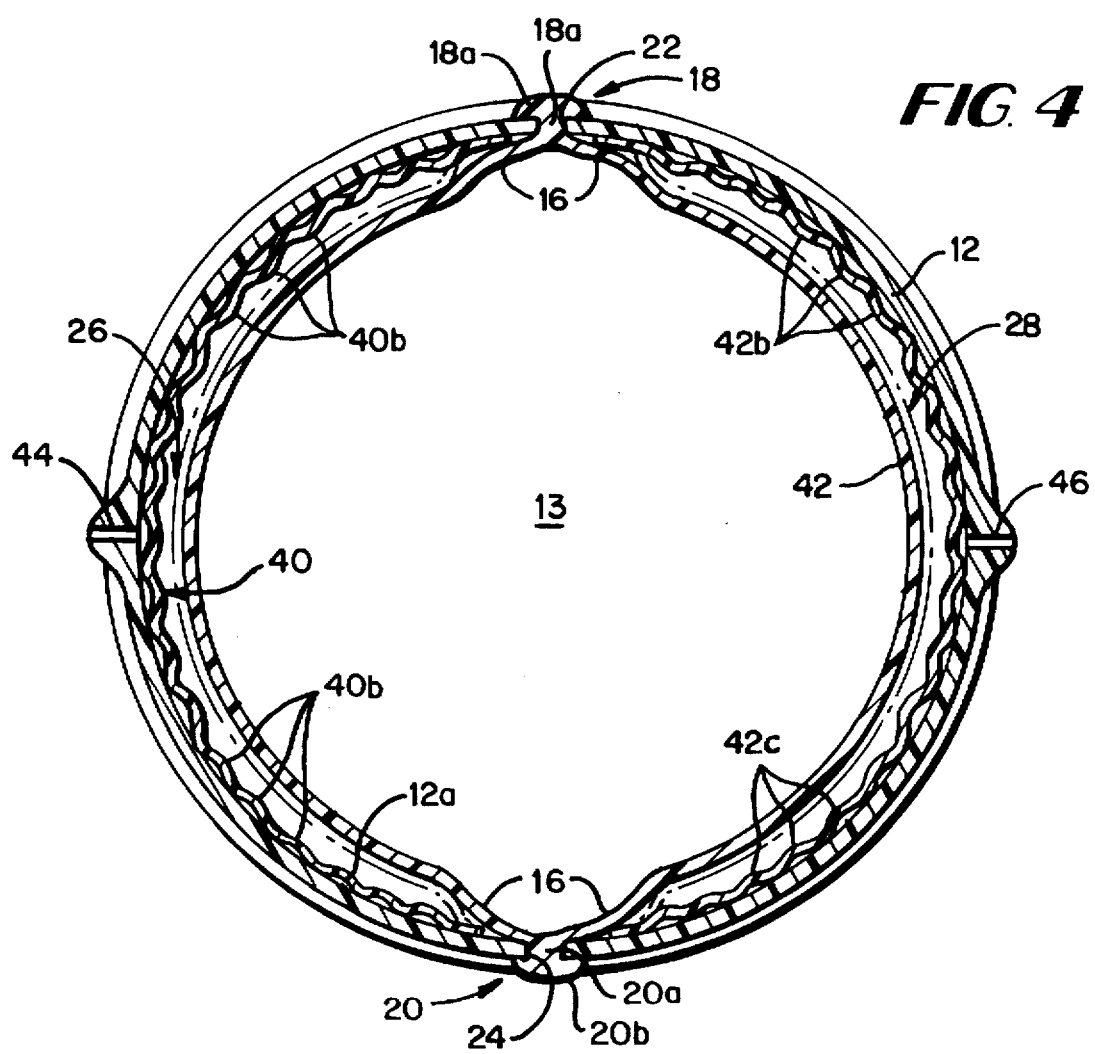

BI-VENTRICULAR CARDIAC ASSIST DEVICE

CROSS-REFERENCE TO RELATED APPLICATIONS

This application is related to, and is a continuation-in-part of, copending U.S. patent application Ser. No. 08/655,310 filed on May 21, 1996, pending which in turn is a continuation of Ser. No. 08/292,726 filed on Aug. 18, 1994 (now abandoned), the entire content of each prior filed application being expressly incorporated hereinto by reference.

GOVERNMENT RIGHTS STATEMENT

This invention was made with Government support under Grant No. HL-48618 awarded by the National Institutes of Health. The Government has certain rights in the invention.

FIELD OF INVENTION

The present invention relates generally to the field of cardiac assist devices, and more particularly, to a direct, mechanical, bi-ventricular cardiac assist device for mechanically actuating the ventricles of a patient's heart.

BACKGROUND OF THE INVENTION

It is common practice today to use mechanical devices to maintain a supply of oxygen and blood circulation during heart failure. One type of device used for this purpose is known as the heart-lung machine. A heart-lung machine performs the function of the heart and lungs. Venous blood is removed from the patient's body and passed through an external oxygenator. The oxygenated blood is then returned to the patient's body. Heart-lung machines are frequently used during open-heart surgery to maintain a supply of oxygen and blood circulation.

Another method which is used to maintain blood circulation is a ventricular actuation cup. These devices typically comprise a cup which fits around the human heart. A thin membrane is bonded to the inner surface of the cup and functions as a diaphragm. Positive and negative pressure is applied to the space between the membrane and the cup wall to alternately inflate and deflate the diaphragm. When the diaphragm is inflated, the heart is squeezed to simulate systolic action. Similarly, when the diaphragm is deflated, the heart muscle relaxes to simulate diastolic action.

The ventricular actuation cups described above have been proven effective in the treatment of patients subject to heart failure. The blood circulation of such patients can be maintained for periods up to several weeks with such devices. However, ventricular actuation cups have some drawbacks.

One frequently encountered problem with the present ventricular actuation cups currently in use relates to the possibility of the failure of the diaphragm. In prior art designs, the diaphragm is bonded to the inner surface of the cup. During the systolic pumping phase, the diaphragm is progressively distended. Several stress factors localized at the bond zones are significantly increased in magnitude. The stress factor associated with a lifting or tearing force at the bond zone reaches its maximum value at maximum systolic distention. This lifting/tearing vector tends to separate the membrane from the cup wall. Continued cyclic development of this stress vector may lead to bond failure which renders the device inoperative. When a bonding failure occurs, the patient's life becomes seriously threatened.

Another significant drawback of currently available ventricular actuation devices is that right and left ventricle pumping is accomplished by using a single diaphragm. As a result, it is difficult to simulate the normal heart function. It is well established that differences exist between right and left ventricle output. It is known, for instance, that right and left ventricular pressures are different. Normal ventricle pressures are 120 over 12–15 mm Hg for the left ventricle and 25–30 over 0–5 mm Hg for the right ventricle. As a result, the pressure selected for ventricular actuation will, at best, be a compromise between the optimum pressure for either the left or right ventricle. Any adjustment of-left ventricular flow or pressure will alter right ventricular pumping parameters. Thus, it is virtually impossible to achieve optimum output and pressures for both the right and left ventricle using a single diaphragm.

The design of currently available ventricular actuation cups also leads to trauma of tissue and organs surrounding the heart. Most cups have a large port molded to the outer surface of the cup which is used for actuation of the diaphragm. When the cup is positioned to contain the heart, the combined reaction to the continuous systolic/diastolic pumping action causes the cup to continually oscillate about its longitudinal axis. The magnitude of this longitudinal oscillation can vary from as much as +15° to −15°. As the device oscillates, the relatively high profile inlet port rubs against surrounding tissue and lungs. The continuous rubbing or abrasion of lung tissue may lead to progressive development of atelectasis in which the alveolar cells in the traumatized lung tissue collapse. In the most serious cases, the continuous trauma has resulted in pulmonary bleeding with resultant pulmonary function compromise.

Another consideration that existing ventricular actuation cups often fail to take into account is the variation in size of the human heart from one person to another. Furthermore, it is possible that different size cups may be needed for the same patient. Certain physiological conditions, such as pulmonary hypertension can result in dilation of the heart. When the ventricular actuation cup is initially placed, a relatively large cup may be needed to accommodate the dilated heart. As the heart returns to a more normal size, the efficiency of the oversize cup in maintaining blood circulation may diminish to the point that a smaller cup must be used. This problem is usually addressed by manufacturing cups of different size to accommodate different size hearts. The surgeon must therefore have a relatively large number of differently sized cups on hand to select from depending on the size of his patient's heart and the patient's physiological condition.

Current univentricular devices, e.g. Anstadt, U.S. Pat. No. 5,119,804 (incorporated herein by reference), presently use a rotary vane combination pressure-vacuum pump as the common source for obtaining and maintaining the pressures and vacuums required for systolic and diastolic ventricular cup actuation. Systolic and diastolic pumping action times are essentially controlled by a combination of timers operating solenoid valves in both the pressure and vacuum lines such that the single drive line delivers a timed sequence of diaphragm distending systolic pressure pulses and diaphragm retraction diastolic vacuum pulses.

An unavoidable requirement in this type of drive line source is a mechanical device called a "damper valve" in the primary drive line exiting the sequencing pressure-vacuum manifold. This valve serves the primary function of "damping" the transition from systolic-diastolic pumping action, in order to prevent diaphragm "slap" during diastolic relaxation. The damper valve is also used in establishing the pressure profile of systolic pumping action e.g. applying during early systolic compression approximately 25–30 mm Hg and during late systolic compression approximately 120–150 mm Hg. Similarly, during the diastolic phase of each cycle, vacuum pressures of approximately −100 to −120 mm Hg are applied.

The requirement of the damping valve for purposes just set forth totally prohibits simultaneous and independent control of both left and right ventricular pumping action, in terms of required physiological flow rates and pressures, and related to patient forward flow requirements of a changing nature with time.

SUMMARY OF INVENTION

The present invention is especially embodied in a bi-ventricular cardiac assist device for maintaining blood circulation in a patient having a minimally functioning or malfunctioning heart. More specifically, the biventricular cardiac assist device of this invention includes a self-supporting cup-shaped outer shell having opposed upper and lower ends, and an inner surface which establishes an interior cavity for receiving a heart therein. The outer shell defines a pair of diametrically opposed slots oriented generally longitudinally between the upper and lower ends of the outer shell. An annular diaphragm conformably shaped to the outer shell is positioned adjacent to the outer shell's inner surface. The diaphragm most preferably includes upper and lower edges bonded to the outer shell at the upper and lower ends thereof, and a pair of diametrically opposed, generally longitudinally oriented unitary connection flange. Each connection flange is preferably generally T-shaped in cross-section and coupled to a respective one of the slots. The connection flanges are thus bonded to the outer shell so that the diaphragm defines a pair of semi-annular fluid chambers with the inner surface of said outer shell.

Most preferably, all structural components, e.g., the outer shell and the diaphragm, are formed of substantially the same urea-linked polyureathane copolymer, but have different Shore A hardness values. The structural components of this invention may thus be isotropically bonded to one another with a liquid bonding agent which is of the same urea-linked polyureathane copolymer. Upon curing, therefore, the various structural components will be unitarily joined with one another so as to provide seamless (and hence structurally integrated) coupling.

These and other aspects and advantages of this invention will become more clear after careful consideration is given to the detailed description of the preferred exemplary embodiments thereof which follow.

BRIEF DESCRIPTION OF THE DRAWINGS

Reference will hereinafter be made to the accompanying drawings wherein like reference numerals throughout the various FIGURES denote like structural elements, and wherein;

FIG. 3 is a partial cross-sectional downward-looking plan view of the cardiac assist device shown in FIG. 2 as taken along lines 3—3 therein;

FIG. 4 is a cross-sectional upward-looking plan view of the cardiac assist shown in FIG. 2 as taken along lines 4—4 therein.

DETAILED DESCRIPTION OF THE PREFERRED EXEMPLARY EMBODIMENTS

I. Structures and Functions

Figure 1:
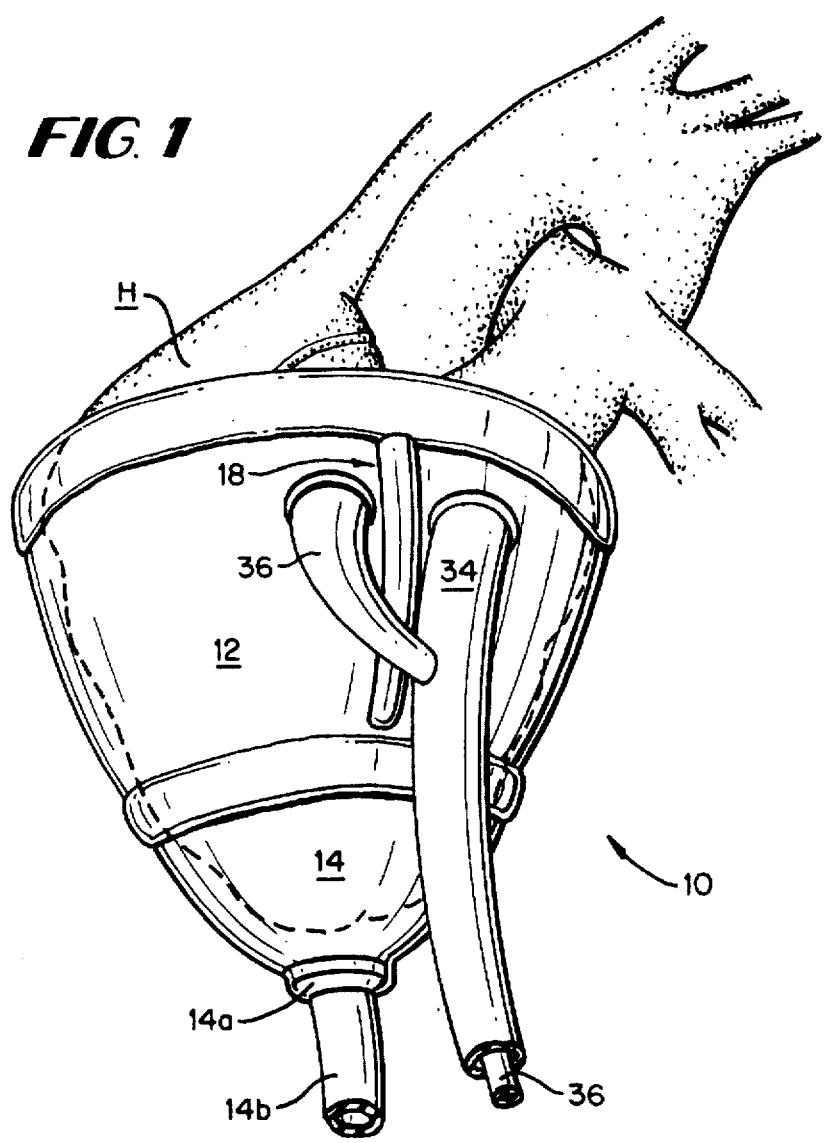
FIG. 1 is an elevational perspective view showing a preferred embodiment of the bi-ventricular cardiac assist device operatively positioned relative to a patient's heart.

As shown particularly in accompanying FIG. 1, the biventricular cardiac assist device 10 according to the present invention generally includes a parabolic-shaped, self-supporting, open-ended, cup-shaped outer shell 12 which defines an upper opening 13 (see FIG. 2) sized and configured to receive a patient's heart H therewithin so that the outer shell 12 substantially entirely bounds the heart's pericardium. The lower open end of the exterior cup member is closed by a self-supporting apical end cap 14 which is sized and configured to receive therewithin the pericardium apex of the patient's heart H.

Figure 2:
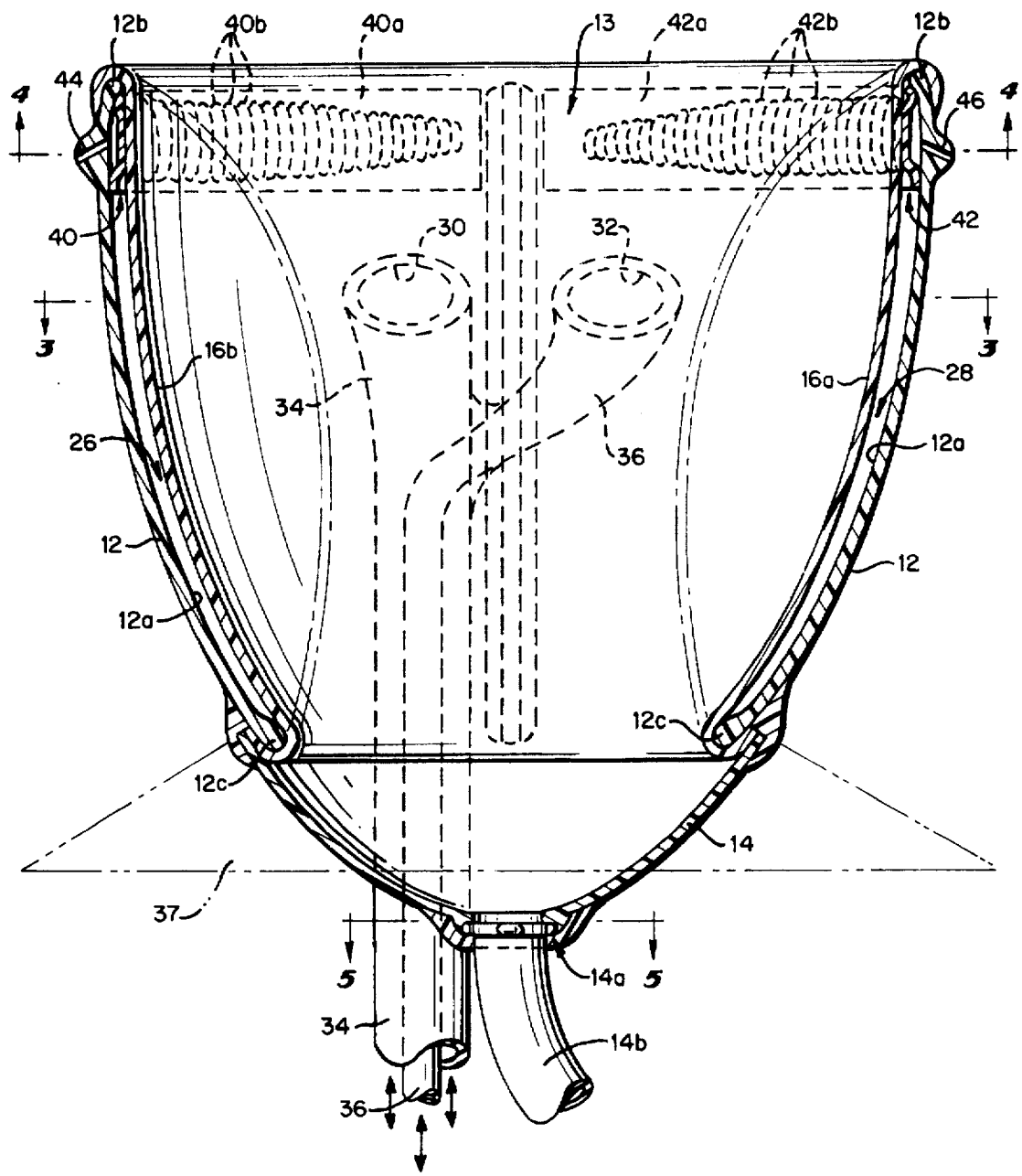
FIG. 2 is a cross-sectional elevational view of the assist device according to this invention.

As is perhaps more clearly shown in accompanying FIGS. 2–4, the device 10 according to this invention is provided with a flexible unitary (i.e., one-piece) annular diaphragm 16 which is conformably shaped to the generally parabolic-shape of the interior surface 12a of cup member 12. In this regard, the upper and lower ends of the diaphragm 16 are wrapped around upper and lower beads 12b, 12c, respectively, of the cup member 12 and are bonded thereto in the manner to be described in greater detail below.

The diaphragm 16 is provided with diametrically opposed, longitudinally oriented (i.e., relative to the elongate central axis of the device 10) T-shaped connection flanges 18, 20. The connection flanges 18, 20 are each most preferably unitarily comprised of a longitudinally oriented central web 18a, 20a, and a cross-flange 18b, 20b oriented at substantially right angles to the web 18a, 20a, respectively. Each of the webs 18a, 20a is received within a longitudinally oriented slot 22, 24 defined in the cup member 12 so that the cross-flange 18a, 18b extends laterally from the slot 22, 24 against the exterior surface of the cup member 12. The entire lengthwise extent of the cross-flanges 18b, 20b may then be bonded to the exterior surface of the cup member 12. In such a manner, therefore, the diaphragm 16 will be provided with an opposed pair of semi-annular flexible diaphragm regions 16a, 16b which define respective closed pressure chambers 26, 28 with the interior surface 12a of the cup member 12 (see FIG. 2).

A pair of inlet openings 30, 32 are formed in the cup member 12 (see FIGS. 2 and 3) and communicate with a respective one of the pressure chambers 26, 28. Each of the openings 30, 32 is fluid-connected to the terminal end of a respective pressure conduit 34, 36. The terminal end of the pressure conduits 34, 36 include an annular flange 34a, 36a, respectively, for purposes of bonding attachment to the exterior surface of the cup member 12 (e.g., as shown by the regions 34b, 36b). The pressure conduits 34, 36 are most preferably elliptically shaped in cross-section so as to exhibit a generally flat profile against the exterior surface of the cup member 12. Moreover, the major extent of the pressure conduit 36 is coaxially disposed within the pressure conduit 34 so as to minimize the component structures close to the patient's organs when in use. As shown, the terminal end of the conduit 36 branches laterally through the wall of the conduit 34 at a position physically near the openings 30, 32. A fluid-tight seal is formed around the penetration area of the conduit 36 by a bonding polymer. Most preferably, the conduits 34, 36 are fluid-connected at their proximal ends to a peristaltic pressure drive system as described more fully in the above-cited U.S. patent application Ser. No. 08/655,310. Each of the diaphragm regions 16a, 16b is therefore capable of being distended into the position shown by phantom lines in FIG. 2 so as to apply pressure against the patient's heart and therefor encourage a mechanically assisted pumping action.

Figure 5:
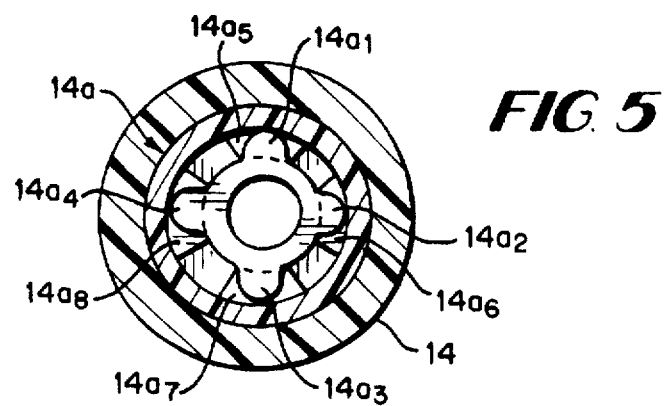
FIG. 5 is a cross-sectional plan view as taken along line 5—5 in FIG. 2 of a multilobe twist connector that may be employed to couple a vacuum conduit to the apical end cap.

The apical end cap 14 terminates in a quick-disconnect coupling 14a to which a flexible conduit 14b is fluid-connected. As shown in FIG. 5, the quick-disconnect coupling 14a is provided by a number of equidistantly spaced apart lobes $14a_1$–$14a_4$ radially extending from the terminal end of conduit 14b so as to provide a male component of the coupling 14a. The other (female component) of the coupling 14a is integrally provided at the lower end of the apical end cap 14 and includes equidistantly spaced apart, radially protruding lands $14a_5$–$14a_8$. Therefore, the lobes $14a_1$–$14a_4$ may be inserted through respective ones of the spaces defined between the lands $14a_5$–$14a_8$ so that, upon effecting a relative quarter-turn rotation therebetween, the lobes $14a_1$–$14a_4$ will rest upon the lands $14a_5$–$14a_8$ and thereby prevent withdrawal of the conduit 14b from the apical end cap 14.

The conduit 14b serves to draw a vacuum within the apical end cap 14 during initial use of the device 10 (e.g., for a period of between 5–7 days) so as to positionally maintain the device 10 during its mechanically assisted pumping action. That is, the vacuum being drawn through the conduit 14b positionally retains the pericardium apex within the apical end cap 14 so as to prevent relative movement between the patient's heart H and the outer shell 12 during mechanical pumping and thereby maintain the heart H properly positioned within the interior of the outer shell 12 at all times during use. In such a manner, therefore, the apical cap 14 and its associated fluid connection via conduit 14b so as to draw a vacuum on the pericardium apex permits the device 10 of this invention to be used without necessarily employing sutures to surrounding non-vascular tissue in order to positionally retain the heart H within the outer shell 12 during mechanical pumping operation. However, if longer term use of the device 10 is desired, then a truncated, generally conically shaped suture skirt 37 may be provide as shown in dashed line in FIG. 2. Preferably the suture skirt 37 is formed of the same material as the outer shell 12 and diaphragm 16 so as to allow isotropic bonding to the lower end of the outer shell 12 by means of the same liquid bonding polymer.

The cardiac assist device 10 of this invention is most preferably provided with a pair of semi-annular compensation cuffs 40, 42 positioned within the chambers 26, 28, respectively near the upper open end 13 of the outer shell 12 (i.e., between the upper ends of the diaphragm regions 16a, 16b and the interior surface 12a of the outer shell 12). The compensation cuffs 40, 42 are most preferably formed as a one piece rectangular strip of flexible elastomeric material having a peripheral region 40a, 42a, respectively, which is bonded in a fluid-tight manner to the interior surface 12a of the outer shell 12.

A number of adjacent, vertically oriented, semi-annular bladder segments (a few of which are identified by reference numerals 40b, 42b, respectively) are therefore bounded by the peripheral regions 40a, 42a and define respective individual vertically oriented semi-annular chambers 40c, 42c which are mutually fluid-connected to one another. In latitudinal cross-section, therefore, the bladder segments 40b, 42b establish an undulating surface (e.g., as can be seen in FIG. 4) when the compensation cuffs 40, 42 are in a deflated condition.

Self-sealing (i.e., one-way) fill valves 44, 46 are provided as an integral part of the outer shell 12 to allow the injection of fluid (e.g., air introduced by a syringe) into the chambers 40c, 42c of the bladder segments 40b, 42b to thereby inflate the compensation cuffs 40, 42 to their respective distended position (shown in phantom lines in FIG. 4). In such a manner, the compensation cuffs 40, 42 will urge the diaphragm regions 16a, 16b into contact with the patient's heart so as to allow the size of the cup opening 13 to be adjusted in dependence on the size of the patient's heart.

It will also be observed, for example in FIG. 2, that the longitudinal extent of the bladder segments 40b, 42b at the opposed terminal ends of the bladders 40, 42, respectively, gradually symmetrically decrease so as to provide a general taper in the direction of the slots 22, 24 of the outer shell 12 (i.e., the bladder segments 40b, 42b at the terminal ends gradually decrease in volumetric capacity from bladder segment to bladder segment toward the slots 22, 24). This gradual taper (lesser volumetric capacity) of the bladder segments 40b, 42b ensures that the bladders 40, 42 will be distended a maximum amount at their respective midpoints to thereby cause the opening 13 of the outer shell 12 to assume a more or less elliptical configuration. In such a manner, therefore, the cup opening 13 more closely conforms to the external cross-sectional anatomy of the patient's heart.

II. Materials of Construction

Preferably, all structural components of the cardiac assist device described previously are formed of a urea-linked polyureathane copolymer which will hereinafter be referred to as "DURAMER" polymer. Bonding between the structural components is accomplished using a liquid polymer of the same formulation. After the bonding polymer is applied and allowed to cure, no seams exist since the bonding polymer and the structural members to which it is applied for purposes of bonding become a unitary, homogeneous and isotropic structure due to the identical material formulation.

The polyureathane block copolymer selected as the base component for use in polymer formulations for the components of the cardiac assist cup device 10 is most preferably an oligomeric diaminobenzoate. Oligomeric diaminobenzoates are readily capable for use in polyureathane cast elastomers because their reactivity is different from that of other MDI-amine formulations commonly used in reaction injection molding (RIM) applications.

Conventional approaches to the preparation of cast elastomers involve the reaction of a short-chain diamine with a long-chain polymer terminated with, usually, toluene diisocyanate. Another commonly used system involves reacting diols with resins capped with methylene-diisocyanate (MDI), or methylene-bis-p-phenyl-isocyanate. The specific method used is dictated by the required physical properties of the product.

Chain extension is accomplished by using MDI, modified forms of monomeric MDI, or MDI containing resins as the hard segment. For chain extension, in addition to the preferred MDI, modified form of monomeric MDI or MDI-containing resins, any suitable organic diisocyanate may be used in the process of this invention such as, for example, aliphatic diisocyanates, aromatic diisocyanates, alicyclic diisocyanates, and heterocyclic diisocyanates including such as, for example, ethylene diisocyanate, ethylidene diisocyanates, propylene diisocyanate, butylene diisocyanate, cyclopentylene-1,3-diisocyanate, cyclopentylene-1,4-diisocyanate, cyclopentylene-1,2-diisocyanate, 2,4-tolylene diisocyanate, 2,6-tolylene diisocyanate, 4,4-diphenylmethane diisocyanate, 2,2-diphenylmethane diisocyanate, 4,4'-diisocyanate, p-phenylene diisocyanate, m-phenylene diisocyanate, xylylene diisocyanate, 1,4-napthylene diisocyanate, 1,5-napthylene diisocyanate, diphenyl-4,4'diisocyanate, azobenzene-4,4'-diisocyanate, diphenylsulfone-4,4'-diisocyanate, dichlorohexamethylene diisocyanate, tetramethylene diisocyanate, pentamethylene diisocyanate, hexamethylene diisocyanate, 1-chlorobenzene-2,4-diisocyanate, furfurylidene diisocyanate, triphenyl methane triisocyanate and the like.

Oligomeric diaminobenzoates reverse the typical arrangement of the reacting species and have the amine functionality capped onto the ends of the soft segment. Elastomers prepared from these formulations exhibit the best overall physical properties of cast, thermoset elastomers, although other soft segments can be used—polyester, polycarbonate, or polypropylene glycol. TDI-amine elastomers contain urethane and urea linkages, while MDI-polyol elastomers contain only urethane linkages. MDI-polyamine elastomers contain only urea linkages.

Specifically, the preferred elastomer components for the practice of the invention fall into three basic classes of components. They are generically described as:

1) Base component (soft chain component): Oligomeric diaminobenzoates (Other soft chain components, e.g., polyether, 1,4 BDO, polyester, polypropylene, and polypropylene glycol, to name a few—can also be used for the molecular structure "back-bone.")

2) Chain extenders: (used to control quality of flexibility, hardness, strength):

a) Diphenylmethane diisocyanate; and
   b) Modified 4,4'-diphenylmethane diisocyanate, as well as others to be later described).

3) Reaction and characteristics modifiers:

a) Methyl ethyl ketone (MEK);
   b) Ethyl alcohol;
   c) polyesters;
   d) polyethers;
   e) glycols; and
   f) polyols.

III. Process and Methodology—Duramer polymer/elastomers

The development of processes for fabricating the Duramer polymer/elastomers used in fabrication of the major assembly components of the cardiac assist device is well founded in the principles of stoichiometric chemistry. Essentially, this chemistry enables the following determinations required for formula development:

1) The NCO % of any MDI polymerizer and the total equivalents of any "back-bone" pre-polymer enable exact determinations of the volume ratios required for 100% polymerization to occur.

2) Hardness or flexibility are essentially controlled by the NCO % of the MDI polymerizer.

3) Considerable latitude in obtaining the desired physical properties of polymer/elastomer are available by the use of the following:

a) reaction modifiers;
   b) stoichiometric balanced mixes of more than one MDI component polymerizer; and/or
   c) stoichiometric balanced mixes of more than one pre-polymer chain component.

Practice of these principles is well-known to those versed in the science of stoichiometric chemistry.

The following Table I identifies the presently preferred physical properties for the Duramer polymer which result in the best possible hemodynamic response during in vitro and in vivo pumping:

TABLE I

| Physical Properties | Outer shell 12 | Diaphragm 16 |
| --- | --- | --- |
| Hardness - Shore A | 78 | 48 |
| Modulus - psi 100% | 980 | 478 |
| Modulus - psi 300% | 1200 | 717 |
| Tensile Strength - psi | 4850 | 3490 |
| Elongation, % | 210 | 488 |
| Tear Strength - pli Die C | 380 | 210 |
| Tear Strength - pli Split | 110 | 85 |
| Rebound - % @ Immediate Release | 68 | 50 |
| Thickness - in. | 0.040 | 0.025 |

IV. Typical Component Fabrication Processed—Examples

The preferred formula components, and their commercial sources include:

1) oligomeric diaminobenzoate A ("OLDA"): Versalink 1000 —Air Products & Chemicals Inc.

2) oligomeric diaminobenzoate B ("OLDB"): Versalink 650 —Air Produce & Chemicals Inc.

3) polyether polyol Multranol 9109—Bayer-Mobay, Pittsburgh, Pa.

4) MDI-4,4'-Diphenylmethane diisocyanate
   a) NCO %=33%: Rubinate PBA-9225 MDI, ICI, Sterling Hts, Mich.
   b) NCO %=8.82: SME-90A, Air Products, Lehigh Valley, Pa., and Baytec MP-090, Bayer-Mobay, Pittsburgh, Pa.
   c) NCO %=5.2: SME-80A, Air Products, Inc., and Baytec—MP-080, Bayer-Mobay
   d) NCO %=3.8: SME-75A, Air Products, inc. and Baytec—MP-075, Bayer-Mobay The following summarizes typical processes used in formulas developed for fabrication of the 3 major assembly components associated with the complete cardiac assist device.

(A) Outside Shell (Outer shell 12)

Example 1A: Liquid pre-polymer/polymerizer solution was prepared with the following volume ratios:

a) (OLDB-A) oligomeric diaminobenzoate-type A—20 cc.
   b) (OLDB-B) oligomeric diaminobenzoate-type B—12 cc.
   c) MDI-NCO=33%, 8 cc.
   d) Methyl ethyl ketone (MEK) 4 cc.

The components were thoroughly mixed-degassed for 3 minutes at vacuum of −30 in Hg—and then mold poured. Mold temperature cure cycle was a) R-T—4 hrs.
   b) 50° C.—6 hrs.

Upon completion of cure cycles—component was removed from mold and set aside for quality control and assembly. The component exhibited a Shore A Hardness of 78–80.

Example 2A: The process of Example 1A was repeated under the following conditions:

a) OLDB-A—20 cc
   b) OLDB-B—12 cc
   c) Polyetherpolyol 12 cc
   d) MDI (NCO=33%) 9 cc
   e) MEK 3.5 cc
   Resultant Shore A Hardness=70–72.

Example 3A: The process of Example 1A was repeated under the following conditions:

a) OLDB-A—22 cc
   b) OLDB-B—10 cc c) Polyetherpolyol 10 cc
d) MDI (NCO=33%) 9 cc
e) MEK 3.5 cc
Resultant Shore A Hardness=65–67.
(B) Inside Flexible Diaphragm (Annular Diaphragm 16)
Example 1B: Liquid pre-polymer/polymerizer solution was prepared with the following volume ratios:
a) OLDB-A—21 cc
b) Modified MDI (NCO %=8.82) 18 cc
c) dibutyl adipate 3.0 cc
d) MEK 2.5 cc
Mixing—degassing, and mold pouring were essentially as previously described above with Example 1A.
Temp cycle: R—T>8 hrs.
50° C.>10 hrs.
The resulting material had a Shore A Hardness of 65–67.

Example 2: The process of Example 1B was repeated under the following conditions:
a) OLDB-A—20 cc
b) Modified MDI (NCO %=8.8) 8 cc
c) Modified MDI (NCO %=10.1) 8 cc
d) dibutyl adipate 4.0 cc
e) MEK 2.5 cc
Shore A Hardness=55–57.

Example 3: The process of Example 1B was repeated under the following conditions:
a) OLDB-A 18 cc
b) Modified MDI (NCO %=5.2) 15 cc
c) Modified MDI (NCO %=3.8) 15 cc
d) MEK 3.0 cc
Temp cycle: R—T>6 hrs.
50° C.>12 hrs.
Shore A Hardness=60–62.

(C) Apical End Cap 14

Typically, the apical end-cap material is formulated to formulas associated with the materials for the "outside shell" (outer shell 12), i.e., Shore A Hardness of 70–80, described previously.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A biventricular cardiac assist device comprising:
   (a) a self-supporting cup-shaped outer shell having opposed upper and lower ends, and an inner surface which establishes an interior cavity for receiving a heart therein;
   (b) a diametrically opposed pair of slots oriented generally longitudinally between said upper and lower ends of said outer shell;
   (c) an annular diaphragm conformably shaped, and disposed adjacent, to said inner surface of said outer shell;
   (d) said diaphragm including upper and lower edges bonded to said outer shell at said upper and lower ends thereof; and
   (e) said diaphragm including a diametrically opposed, generally longitudinally oriented connection flanges each coupled to a respective one of said slots and bonded to said outer shell so that said diaphragm defines a pair of semi-annular fluid chambers with said inner surface of said outer shell.

2. The device of claim 1, wherein said connection flanges integrally include a cross flange, and a longitudinally oriented central web having a proximal end coupled to said diaphragm and a distal end coupled to said cross-flange.

3. The device of claim 2, wherein said connection flanges are generally T-shaped in cross-section.

4. The device of claim 1, wherein said upper and lower edges and said connection flanges of said diaphragm are bonded to said exterior surface of said outer shell with a bonding agent.

5. The device of claim 4, wherein said bonding agent is an isotropic bonding agent which forms a unitary structure between said diaphragm and said shell.

6. The device of claim 5, wherein said diaphragm, said outer shell and said bonding agent are each formed of substantially the same urea-linked polyureathane copolymer.

7. The device of claim 1, further comprising a apical end cap closing said lower end of said outer shell.

8. The device of claim 7, wherein said apical end cap includes a vacuum port for connection with a source of vacuum.

9. The device of claim 8, wherein said vacuum port includes a multilobe disconnect structure.

10. The device of claim 1, further comprising an annular suture skirt extending outwardly from said lower end of said outer shell.

11. The device of claim 1, further comprising a pair of semi-annular compensation cuffs disposed between said diaphragm and said interior surface of said outer shell near said upper end thereof.

12. The device of claim 11, wherein each of said compensation cuffs includes a plurality of adjacent, longitudinally oriented, semi-annular bladder segments defining respective individual vertically oriented semi-annular chambers which are mutually fluid-connected to one another.

13. The device of claim 12, wherein each of said compensation cuffs includes a peripheral region bonding said bladder segments which is bonded in a fluid-tight manner to said interior surface of said outer shell.

14. The device of claim 11 or 13, wherein said outer shell includes a self-sealing one-way fluid-injection port for allowing fluid to be introduced into said compensation cuffs.

15. The device of claim 11 or 13, wherein each of said compensation cuffs includes opposed tapered ends so that said compensation cuffs distend a maximum amount at their respective midpoints to thereby create a generally elliptical opening into said upper end of said outer shell.

16. The device of claim 1, wherein said outer shell includes a pair of pressure ports each in fluid-communication with a respective one of said fluid chambers.

17. The device of claim 16, further comprising a pair of fluid conduits each having a distal end coupled to a respective one of said pressure ports.

18. The device of claim 17, wherein said fluid conduits are generally coaxial so that one of said conduits is physically positioned within another of said conduits, and wherein said one of said fluid conduits has a branch near said distal end thereof which extends outwardly through said another of said conduits.

19. The device of claim 17 or 18, wherein said fluid conduits each have a generally elliptical cross-section and are bonded to said exterior surface of said outer shell.

20. A cardiac assist device comprising:
   a cup-shaped outer shell having upper and lower ends; and
   a flexible diaphragm conformably shaped to and disposed on an interior of said outer shell; wherein said flexible diaphragm includes upper and lower edges bonded to upper and lower ends of said outer shell by a bonding agent so as to form an isotropic bond between said upper and lower edges of said diaphragm and said upper and lower ends of said outer shell, respectively; and wherein each of said outer shell, diaphragm and bonding agent is formed of a urea-linked polyureathane copolymer.

21. The device of claim 20, wherein said diaphragm establishes a pair of semi-annular fluid chambers with said outer shell.

22. The device of claim 21, wherein said outer shell includes a pair of diametrically opposed, longitudinally oriented slots, and wherein said diaphragm unitarily includes a pair of diametrically opposed, longitudinally oriented connection flanges bonded to said outer shell.

23. The device of claim 22, wherein said connection flanges integrally include a cross flange, and a longitudinally oriented central web having a proximal end coupled to said diaphragm and a distal end coupled to said cross-flange.

24. The device of claim 23, wherein said connection flanges are generally T-shaped in cross-section.

25. The device of claim 20, wherein said upper and lower edges are wrapped around said upper and lower ends of said outer shell and are bonded to said exterior surface of said outer shell with said bonding agent.

26. The device of claim 20, further comprising an apical end cap closing said lower end of said outer shell and formed of said urea-linked polyureathane copolymer, said apical end cap being bonded to said outer shell by said bonding agent.

27. The device of claim 26, wherein said apical end cap includes a vacuum port for connection with a source of vacuum.

28. The device of claim 27, wherein said vacuum port includes a multilobe disconnect structure.

29. The device of claim 20, further comprising an annular suture skirt extending outwardly from said lower end of said outer shell and formed of said urea-linked polyureathane copolymer, said suture skirt being bonded to said outer shell by said bonding agent.

30. The device of claim 20, further comprising a pair of semi-annular compensation cuffs disposed between said diaphragm and said interior surface of said outer shell near said upper end thereof.

31. The device of claim 30, wherein each of said compensation cuffs includes a plurality of adjacent, longitudinally oriented, semi-annular bladder segments defining respective individual vertically oriented semi-annular chambers which are mutually fluid-connected to one another.

32. The device of claim 31, wherein each of said compensation cuffs includes a peripheral region bonding said bladder segments which is bonded in a fluid-tight manner to said interior surface of said outer shell.

33. The device of claim 31 or 32, wherein said outer shell includes a self-sealing, one-way fluid-injection port for allowing fluid to be introduced into said compensation cuffs.

34. The device of claim 31 or 33, wherein each of said compensation cuffs includes opposed tapered ends so that said compensation cuffs distend a maximum amount at their respective midpoints to thereby create a generally elliptical opening into said upper end of said outer shell.

35. The device of claim 20, wherein said outer shell includes a pair of pressure ports each in fluid-communication with a respective one of said fluid chambers.

36. The device of claim 35, further comprising a pair of fluid conduits each having a distal end bonded to a respective one of said pressure ports by said bonding agent.

37. The device of claim 36, wherein said fluid conduits are generally coaxial so that one of said conduits is physically positioned within another of said conduits, and wherein said one of said fluid conduits has a branch near said distal end thereof which extends outwardly through said another of said conduits.

38. The device of claim 36 or 37, wherein said fluid conduits each have a generally elliptical cross-section and are bonded to said exterior surface of said outer shell.

39. The device of claim 36 or claim 37 wherein said pair of conduits is each formed from said urea-linked polyureathane copolymer.

* * * * *